United States Patent [19]

Light et al.

[11] 4,041,084
[45] Aug. 9, 1977

[54] TRICYCLIC ALCOHOLS

[75] Inventors: Kenneth K. Light, Long Branch, N.J.; Edward J. Shuster, Brooklyn, N.Y.; Joaquin F. Vinals, Red Bank; Manfred Hugo Vock, Locust, both of N.J.

[73] Assignee: International Flavors & Fragrances Inc., New York, N.Y.

[21] Appl. No.: 683,246

[22] Filed: May 5, 1976

Related U.S. Application Data

[63] Continuation-in-part of Ser. No. 485,554, July 3, 1974, abandoned.

[51] Int. Cl.$^2$ ............................................. C07C 35/22
[52] U.S. Cl. ........................... 260/617 F; 131/17 R; 131/17 A; 252/89 R; 252/132; 252/173; 252/522; 260/586 C; 260/586 G; 260/617 R; 424/69; 426/598; 426/650
[58] Field of Search ................................. 260/617 F

[56] References Cited

U.S. PATENT DOCUMENTS

| | | | |
|---|---|---|---|
| 3,879,466 | 4/1975 | Light | 260/617 F |
| 3,907,908 | 9/1975 | Light et al. | 260/617 F |
| 3,925,486 | 12/1975 | Greuter et al. | 260/617 F |

Primary Examiner—Norman Morgenstern
Attorney, Agent, or Firm—Arthur L. Liberman; Harold Haidt; Franklin D. Wolffe

[57] ABSTRACT

Tricyclic alcohol compounds having the formula:

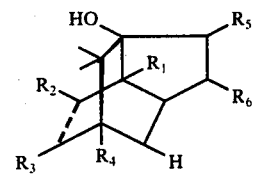

wherein each of $R_1$, $R_2$, $R_3$, $R_4$, $R_5$ and $R_6$ is selected from the group consisting of hydrogen and methyl; wherein the dashed line is a carbon-carbon single bond or a carbon-carbon double bond; and wherein, when the dashed line is a carbon-carbon single bond, one of $R_2$ or $R_3$ is hydrogen; useful in preparing compositions for augmenting or enhancing the flavor and/or aroma of consumable products including foods, tobacco and perfumes.

3 Claims, No Drawings

TRICYCLIC ALCOHOLS

This application is a continuation-in-part of U.S. application for Letters Pat. Ser. No. 485,554, filed on July 3, 1974, now abandoned.

BACKGROUND OF THE INVENTION

Materials which can provide warm, patchouli-like, earthy, camphoraceous and woody fragrance notes are known in the art of perfumery. Many of the natural materials which provide such fragrances and contribute desired nuances to perfumery compositions are high in cost, vary in quality from one batch to another and/or are generally subject to the usual variations of natural products.

There is accordingly a continuing effort to find synthetic materials which will replace the essential fragrance notes provided by natural essential oils or compositions thereof. Unfortunately, many of these synthetic materials either have the desired nuances only to a relatively small degree or else contribute undesirable or unwanted odor to the composition. The search for materials which can provide a more refined patchouli-like fragrance has been difficult and relatively costly in the areas of both natural products and synthetic products.

Buchi et al., 83 J. Am. Chem. Soc. 927 (1961), shows the production of a material called "patchoulione" which is stated to be octahydro-1,4,9,9-tetramethyl-3a,7-methanoazulen-5(4H)-one having the structure:

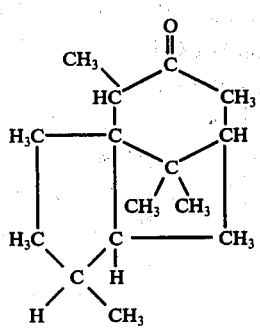

U.S. Pat. No. 3,748,284 issued on July 24, 1973 disclosed perhydro derivatives of methanoazulen as having camphoraceous woody fragrances and having the ability to impart this fragrance to perfumed compositions and perfumed articles. The compounds disclosed are:

a. Octahydro-1,4,9,9-tetramethyl-4,7-methanoazulen-3(2H)-one having the structure:

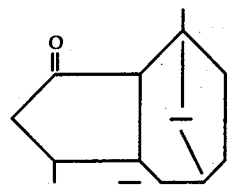

b. Octahydro-1,4,9,9-tetramethyl-4,7-methanoazulen-2(3H)-one having the structure:

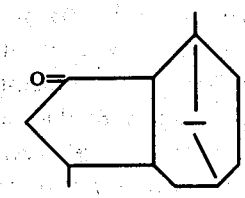

c. Octahydro-1,4,9,9-tetramethyl-4,7-methanoazulen-8(7H)-one having the structure:

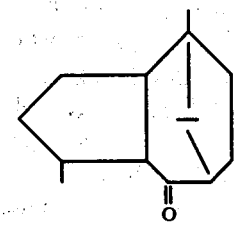

Umarani et al., Sept./Oct. 1969, P. & E.O.R., 307 discloses two compounds relevant to the instant case: "isopatchoulinol" having the structure:

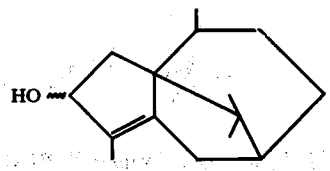

and "patchouli alcohol" having the structure:

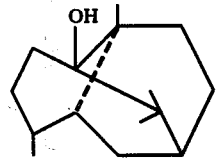

In addition, artifical flavoring agents for food-stuffs have received increasing attention in recent years. In many years, such food flavoring agents have been perferred over natural flavoring agents at least in part due to their diminished cost and their reproducible flavor qualities. For example, natural food flavoring agents such as extracts, concentrates and the like are often subject to wide variations due to changes in the quality, type and treatment of the raw materials. Such variations can be reflected in the end product and result in unfavorable flavor characteristics in said end product. Additionally, the presence of the natural product in the ultimate food may be undesirable because of increase tendency to spoil. This is particularly troublesome in food and food uses where such products as dips, soups, chips, sausages, gravies and the like are apt to be stored prior to use.

The fundamental problem in creating artificial flavor agents is that the artificial flavor to be achieved be as natural as possible. This generally proves to be a difficult task since the mechanism for flavor development in many foods is not completely known. This is noticable in products having nutty, earthy, woody-balsamic, fresh walnut-kernel and walnut-skin flavor characteristics.

Reproduction of nutty, earthy, woody-balsamic, fresh walnut-kernel and walnut-skin flavor and aroma has been the subject of long and continuing searches by those engaged in aproduction of foodstuffs and beverages. The severe shortage of food in many parts of the world has given rise to the development of previously unused sources of protein which are unpalatable. Accordingly, the need has arisen for the use of flavoring materials which will make such sources of protein palatable to human sensory organs.

Even more desirable is a product that can serve to substitute for difficult-to-obtain natural perfumery oils and at the same time substitute for natural flavoring ingredients in both foodstuffs as well as in tobacco.

Mirrington and Schmalzl 37 *J. Org. Chem.* No. 38, 1972, pages 2871-2877 discloses the isolation of (−) patchouli alcohol having the structure:

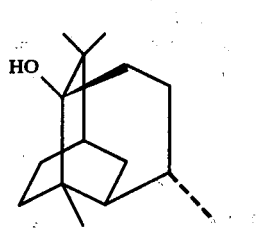

An article by Corey and Wipke entitled "Computer-Assisted Design of Complex Organic Syntheses" appearing in 166 Science 178 (1969) sets forth, interalia, the sequence of reactions leading to compounds having the structures:

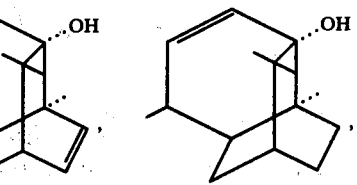

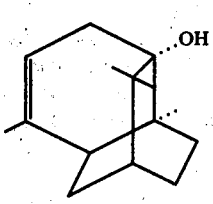

and

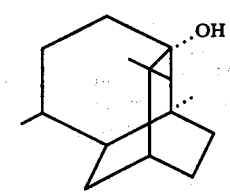

One of these reaction sequences involves performing the reactions:

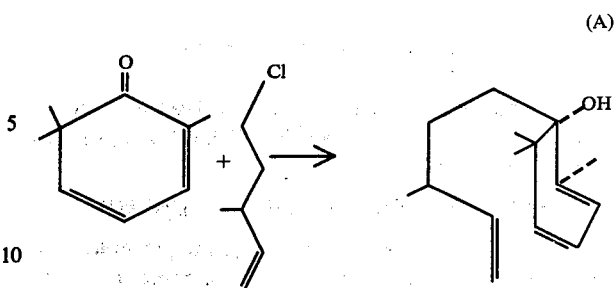
(A)

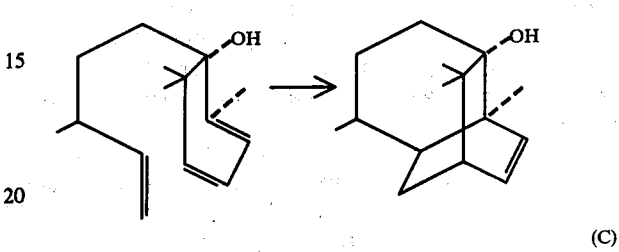
(B)

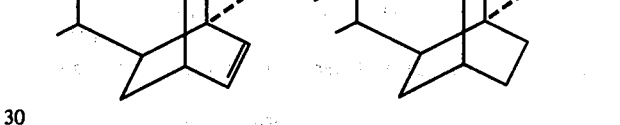
(C)

However, syntheses of lower methylene homologues and double compound isomers and an analogous patchouli alcohol and dihydropatchouli alcohol have not yet been disclosed in the prior art. Indeed, economic syntheses of patchouli alcohol itself do not appear to be given in the literature.

Danishevsky and Dumas 1968 Chemical Communication, Pages 1287-1288 discloses the synthesis of racemic patchouli alcohol and epi patchouli alcohol having the structure:

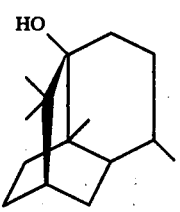

by means of cyclization of a compound having the structure:

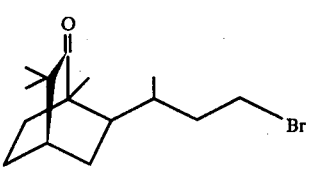

The use in perfumery of the compound having the structure:

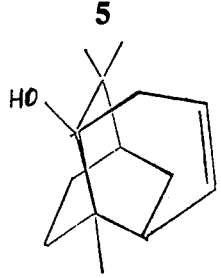

("norpatchoulinol") is disclosed in the following patents:
1. Belgium Pat. No. 788,301 issued Mar. 1, 1973
2. German Offenlegungschrift No. 2,242,913 published Mar. 8, 1973
3. Dutch published Application No. 72/11760 published Mar. 5, 1973

A product of the reduction of this compound is also disclosed norpatchoulinol"). This product has the structure:

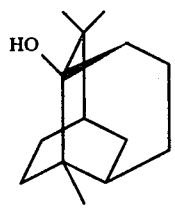

The compounds of our invention have properties considered to be unobvious, unexpected and advantageous with respect to the properties of the above-mentioned prior art compounds.

In addition, application for U.S. Letters Pat. Ser. No. 436,848 filed on Jan. 28, 1974 claims processes and compositions for altering the flavor and/or aroma of consumable products including foods, tobacco and perfumes utilizing as the essential ingredient at least one organic tricyclic alcohol having the formula:

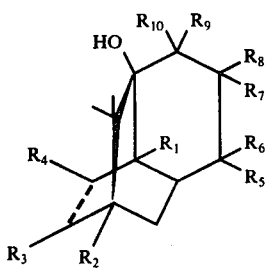

wherein each of $R_1$, $R_2$, $R_3$, $R_4$, $R_5$, $R_6$, $R_7$, $R_8$, $R_9$ and $R_{10}$ is selected from the group consisting of hydrogen and methyl; wherein the dashed line is a carbon-carbon single bond or a carbon-carbon double bond; wherein $R_1$ is limited to hydrogen when (i) the dashed line is a carbon-carbon single bond; (ii) $R_2$, $R_3$, $R_4$, $R_6$, $R_7$, $R_8$, $R_9$ and $R_{10}$ is hydrogen and (iii) $R_5$ is hydrogen or methyl and wherein when the dashed line is a carbon-carbon single bond, one of $R_3$ or $R_4$ is hydrogen; and processes for preparing the above-mentioned compounds and in addition compounds having similar structures; that is, when the dashed line is either a carbon-carbon single bond or a carbon-carbon double bond; $R_1$, $R_2$, $R_3$, $R_4$, $R_6$, $R_7$, $R_8$, $R_9$ and $R_{10}$ are each the same or different and each represents hydrogen and wherein when $R_3$ or $R_4$ is hydrogen the dashed line represents a carbon-carbon single bond and when $R_3$ and $R_4$ are both methyl, the dashed line represents a carbon-carbon double bond, involving first intimately admixing a methyl substituted cyclohexadienone having the structure:

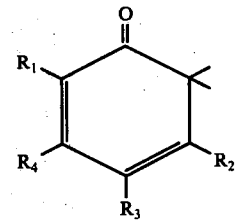

with an acetylenic compound having the structure:

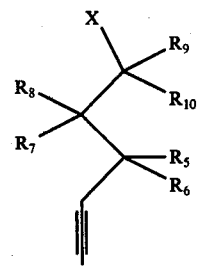

wherein X can be either hydroxyl, bromo or chloro thereby forming a diene compound having the structure:

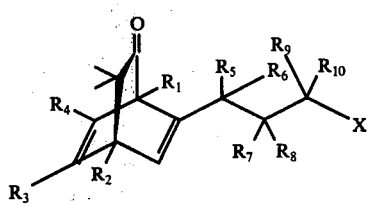

and then hydrogenating the diene compound with hydrogen in the presence of a hydrogenation catalyst whereby producing a ketone having the structure:

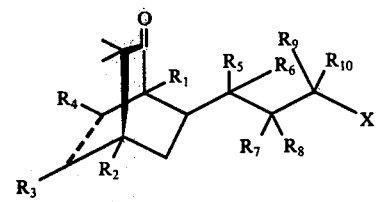

It is further disclosed that this ketone may either be immediately cyclized using an alkali metal such as sodium, potassium or lithium in the case of X being halogen, or when X is OH, the ketone, is first halogenated with a halogenating agent to first form a compound having the structure:

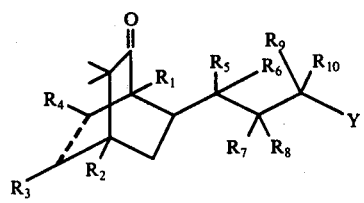

wherein Y is bromo or chloro and subsequently the halogenated compound may then be cyclized using a cyclizing agent.

The compounds, uses and processes claimed in Ser. No. 436,848 filed on Jan. 28, 1974 now Pat. No. 3,907,908, do not contemplate the lower methylene homologues thereof of the instant case.

Furthermore, application for U.S. Letters Pat. Ser. No. 436,847 filed on Jan. 28, 1974 now U.S. Pat. No. 3,879,466, chemical compounds having the structure:

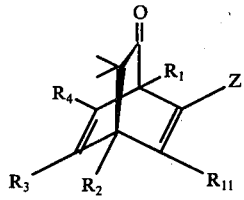

wherein Z is a moiety selected from the group consisting of:

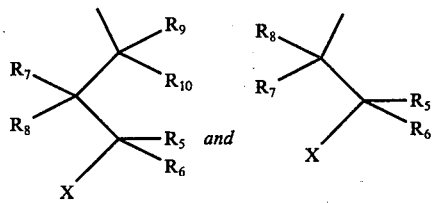

and wherein $R_1$, $R_2$, $R_3$, $R_4$, $R_5$, $R_6$, $R_7$, $R_8$, $R_9$ and $R_{10}$ are the same or different and each is selected from the group consisting of methyl and hydrogen and wherein $R_{11}$ is selected from the group consisting of methyl, ethyl and hydrogen; and wherein X is selected from the group consisting of bromo, chloro, hydroxyl, benzyloxy and alkoxyl and a process for preparing such compounds involving intimately admixing a methyl substituted cyclohexadienone having the structure:

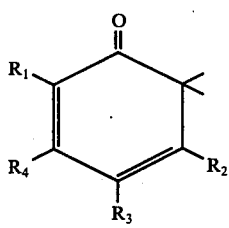

with one of the following acetylenic compounds having the structures:

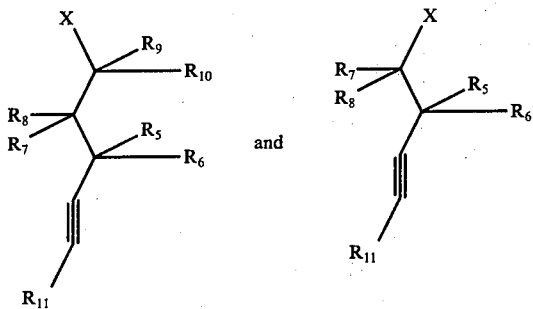

Neither the processes nor the compounds claimed in Ser. No. 436,847 filed on Jan. 28, 1974 now Pat. No. 3,879,466, are encompassed within the scope of the instant invention.

THE INVENTION

It has now been determined that certain tricyclic alcohols are capable of imparting a variety of flavors and fragrances to various consumatle materials. Briefly, our invention contemplates tricyclic alcohols having the structure:

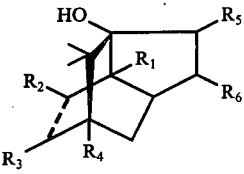

wherein Each of $R_1$, $R_2$, $R_3$, $R_4$, $R_5$ and $R_6$ is selected from the group consisting of hydrogen and methyl; wherein the dashed line is a carbon-carbon single bond or a carbon-carbon double bond; and wherein when the dashed line is a carbon-carbon single bond, at least one of $R_2$ or $R_3$ is hydrogen; useful in augmenting or enhancing the flavors and/or fragrances of such consumable materials.

The tricyclic alcohols of our invention are actually racemic mixtures rather than individual stereoisomers, such as the case concerning isomers of patchouli alcohol which are so obtained from patchouli oil.

A specific example of a novel product which has been found to be particularly useful in perfumery is the compound having the structure:

This compound has a strong patchouli-like, slightly minty, sweet, warm, earthy, camphoraceous note and an earthy, patchouli, nutty and woody-like taste and aroma in food flavors.

The tricyclic alcohols of our invention can be obtained by means of two closely related reaction sequences; set forth below:

The first route comprises first intimately admixing a methyl-cyclohexadienone having the structure:

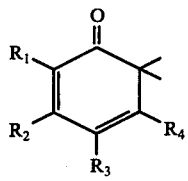

with an acetylenic compound having the structure:

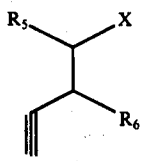

wherein X may be either hydroxyl, bromo and chloro thereby forming a diene compound having the structure:

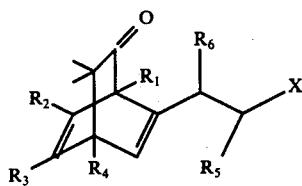

In this reaction, it is best to proceed at a temperature in the range of 170°–260° C with the most preferred temperature range being 200°–210° C. The reaction may be carried out in the presence of an inert solvent such as benzene, hexane or cyclohexane (or any other inert solvent) or the reaction may be carried out in the absence of solvent. Although, either the acetylenic compound or the cyclohexadienone may be used in excess, it is preferred to use equimolar quantities of each reactant.

The above-mentioned diene compound is then hydrogenated with hydrogen in the presence of a catalyst such as palladium, platinum, nickel or other suitable hydrogenation catalyst.

The reaction temperature may be from 20°–220° C with a temperature range of 100°–200° C being preferred.

The reaction is preferably carried out at superatmospheric pressures and pressures in the range of 1–150 atmospheres are suitable. Preferred pressures range from 5–15 atmospheres.

The hydrogenation reaction gives rise to a ketone product having the structure:

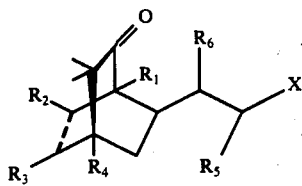

but it is noteworthy that the compound produced is one where the dashed line is a carbon-carbon single bond if one of $R_2$ or $R_3$ is hydrogen and the compound is primarily one where the dashed line is a carbon-carbon double bond if $R_2$ and $R_3$ are both methyl.

When X is halogen, the ketone thus produced may then be immediately cyclized by treating same with an alkali metal selected from the group consisting of sodium, potassium or lithium. The cyclization may be carried out in diethyl ester, tetrahydrofuran or benzene. The reaction temperature preferred as the reflux temperature of the reaction mass at atmospheric pressure and is a function of the solvent used. Thus, for example, when using tetrahydrofuran solvent, the cyclization reaction temperature is approximately 65° C. The reaction can be carried out at temperatures ranging from 0° up to 100° C. For the cyclization, the mole ratio of ketone to metal is preferably 7:1 although mole ratio of ketone to metal is from 1:1 up to 10:1 may be used.

Prior to cyclization, in the event that X is OH, the ketone must be halogenated with thionyl chloride or any other suitable halogenating agent, for example, thionyl chloride-pyridine complex, phosphorous-trichloride, phosphorous-tri-bromide, aqueous HCl or aqueous HBr. The halogenation reaction may be carried out in the presence or in the absence of an inert solvent such as benzene, toluene, cyclohexane or pyridine. The reaction temperature may range from 20° up to 100° C with a reaction temperature of 80° C being preferred. The mole ratio of halogenating agent:ketone of 3:1 is preferred when using thionyl chloride and a ratio of 10:1 is preferred when using aqueous HCl and HBr.

The initial reaction may utilize, for example, the following reactants:
a. Acetylenic compounds:
2-Methylbut-3-yn-1-ol
2-Methylbut-3-yn-1-chloride
2-Methylbut-3-yn-1-bromide
But-3-yn-1-ol
But-3-yn-1-chloride
But-3-yn-1-bromide
2-Chloro-3-methyl-4-pentyne
2-Chloro-4-pentyne
b. Cyclohexadieneone compounds:
2,6,6-Trimethylcyclohexadien-1-one
2,3,4,5,6,6-Hexamethylcyclohexadien-1-one
2,3,4,6,6-Pentamethylcyclohexadien-1-one
6,6-Dimethylcyclohexadien-1-one
4,5,6,6-Tetramethylcyclohexadien-1-one
2,4,5,6,6-Pentamethylcyclohexadien-1-one When the final cyclization reaction is completed, the reaction mixture is "worked-up" using routine purification procedures including the unit operations of extraction, crystallization, drying and/or distillation.

The individual tricyclic compounds of our invention can be obtained in purer form or in substantially pure form by conventional purification techniques. Thus, the products can be purified and/or isolated by distillation, extraction, crystallization, preparative chromatographic techniques, and the like. It has been found desirable to purify the tricyclic compounds by fractional distillation by vacuum.

It will be appreciated from the present disclosure that the tricyclic compounds and mixtures thereof according to the present invention can be used to alter, vary, fortify, modify, enhance or otherwise improve the flavor of a wide variety of materials which are ingested, consumed, or otherwise organoleptically sensed.

The term "alter" in its various forms will be understood herein to mean the supplying or imparting of a flavor character or note to an otherwise bland, relatively tasteless substance, or augmenting an existing flavor characteristic where the natural flavor is deficient in some regard or supplementing the existing flavor impression to modify the organoleptic character.

Such compounds are accordingly useful in flavoring compositions. A flavoring composition is taken to mean one which contributes a part of the overall flavor impression by supplementing or fortifying a natural or artificial flavor in a material or one which supplies substantially all the flavor and/or aroma character to a consumable article.

The term "enhance" is intended herein to mean the intensification of a particular aroma or taste nuance without changing the quality or nature of said nuance and without adding an additional aroma or taste nuance to the consumable material, the organoleptic properties of which are enhanced.

The term "foodstuff" as used herein includes both solid and liquid ingestible materials for man or animals, which materials usually do, but need not, have nutritional value. Thus, foodstuffs includes meats, gravies, soups, convenience foods, malt, alcoholic, and other beverages, milk and dairy products, seafoods including fish, crustaceans, mollusks, and the like, candies, vegetables, cereals, soft drinks, snacks, dog and cat food, other veterinary products, and the like.

The tricyclic compounds of our invention are useful tobacco flavorants and flavor enhancers.

The term "tobacco" will be understood herein to mean natural products such as, for example, burley, Turkish tobacco, Maryland tobacco, flue-cured tobacco and the like including tobacco-like or tobacco-based products such as reconstituted or homogenized leaf and the like, as well as tobacco substitutes intended to replace natural tobacco, such as lettuce and cabbage leaves and the like. The tobaccos and tobacco products in which the tricyclic compounds of our invention are useful include those designed or used for smoking such as in cigarette, cigar and pipe tobacco, as well as products such as snuff, chewing tobacco, and the like.

When the tricyclic compounds of this invention are used in a flavoring composition, they can be combined with conventional flavoring materials or adjuvants. Such co-ingredients or flavoring adjuvants are well known in the art for such use and have been extensively described in the literature. Apart from the requirement that any such adjuvant material be ingestibly acceptable, and thus non-toxic or otherwise non-deleterious, conventional materials can be used and broadly include other flavor materials, vehicles, stabilizers, thickeners, surface active agents, conditioners, and flavor intensifiers.

Such conventional flavoring materials include saturated fatty acids, unsaturated fatty acids and amino acids; alcohols, including primary and secondary alcohols; esters; carbonyl compounds including ketones and aldehydes; lactones; other cyclic organic materials including benzene derivatives, alicyclic compounds, heterocyclics such as furans, pyridines, pyrazines and the like; sulfur-containing materials including thiols, sulfides, disulfides and the like; proteins, lipids, carbohydrates; so-called flavor potentiators such as monosodium glutamate, guanylates, and inosinates; natural flavoring materials such as cocoa, vanilla and caramel; essential oils and extracts such as anise oil; clove oil; and the like; and artificial flavoring materials such as vanillin; and the like.

Specific flavor adjuvants are as follows:
Ethyl-2-methyl butyrate;
Vanillin;
Butyl valerate;
2,3-Diethyl pyrazine;
Methyl cyclopentenolone;
Benzaldehydel;
Valerian Oil Indian; and
Propylene glycol The tricyclic compounds of our invention can be used to contribute warm, patchouli-like, earthy, woody and camphoraceous aromas. As olfactory agents the tricyclic compounds of this invention can be formulated into or used as components of a "perfume composition".

The term "perfume composition" is used herein to mean a mixture of organic compounds, including, for example, alcohols, aldehydes, ketones, nitriles, esters, and frequently hydrocarbons which are admixed so that the combined odors of the individual components produce a pleasant or desired fragrance. Such perfume compositions usually contain: (a) the main note of the "bouquet" or foundation-stone of the composition; (b) modifiers which round-off and accompany the main note: (c) fixatives whch include odorous substances which lend a particular note to the perfume throughout all stages of evaporation, and substances which retard evaporation; and (d)top-notes which are usually low-boiling fresh smelling materials.

In perfume compositions, the individual component will contribute its particular olfactory characteristics but the overall effect of the perfume composition will be the sum of the effect of each ingredient. Thus, the individual compounds of this invention, or mixtures thereof, can be used to alter the aroma characteristics of a perfume composition, for example, by highlighting or moderating the olfactory reaction contributed by another ingredient in the composition.

The amount of the tricyclic compounds of this invention which will be effective in perfume compositions depends on many factors, including the other ingredients, their amounts and the effects which are desired. It has been found that perfume compositions containing as little as 1 percent of the tricyclic compounds of this invention, or even less, can be used to impart a warm patchouli scent with earthy, woody and camphoraceous notes to soaps, cosmetics, and the other products. The amount employed can range up to 50% or higher and will depend on considerations of cost, nature of the end product, the effect desired on the finished product and particular fragrance sought.

The tricyclic compounds of this invention can be used alone or in a perfume composition as an olfactory component in detergents, and soaps, space odorants and deodorants; perfumes; colognes; toilet waters; bath salts; hair preparations such as lacquers, brilliantines, pomades, and shampoos; cosmetic preparations such as creams, deodorants, hand lotions, and sun screens; powders such as talcs, dusting powders, face powder, and the like. When used in an olfactory component of a perfumed article, as little as 0.1 percent of one or more of the tricyclic compounds will suffice to impart a warm patchouli aroma with earthy, woody and camphoraceous notes. Generally, no more than 0.5 percent is required.

In addition, the perfume composition can contain a vehicle or carrier for the tricyclic compounds alone or with other ingredients. The vehicle can be a liquid such as an alcohol such as ethanol, a glycol such as propylene glycol, or the like. The carrier can be an absorbent solid such as a gum or components for encapsulating the composition.

The following examples are given to illustrate embodiments of the invention as it is presently preferred to practice it. It will be understood that these examples are illustrative, and the invention is not to be considered as restricted thereto except as indicated in the appended claims.

EXAMPLE I

PREPARATION OF 3,3-DIMETHYL-6-(2-HYDROXYETHYL)-BICYCLO (2.2.2)-OCTA-5,7-DIEN-2-ONE

A mixture of 50 g of 6,6-dimethylcyclohexadienone and 50 g of 3-butyn-1-ol in 300 ml of benzene is placed in an autoclave and heated to 200°-210° C for 3 hours. The autoclave is then cooled to room temperature and the reaction mixture is removed, the solvent stripped and the residue distilled under vacuum through a 3 inch microvigreaux column yielding 65 g of 3,3-dimethyl-6-(2-hydroxyethyl)-bicyclo(2.2.2)-octa-5,7-dien-2-one having the structure:

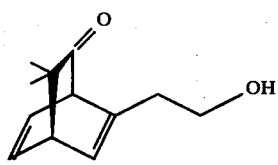

EXAMPLE II

PREPARATION OF 3,3-DIMETHYL-6-(2-HYDROXYETHYL)-BICYCLO (2.2.2)-OCTAN-2-ONE

A mixture of 60 g of 3,3-dimethyl-6-(2-hydroxyethyl)-bicyclo(2.2.2)-octa-5,7-diene-2- one produced according to Example I, 300 ml of isopropyl alcohol and 5 g of 5% palladium an charcoal catalyst is placed in an autoclave. The autoclave is pressurized with hydrogen and heated to 100° C for 6 hours. The resulting reaction mixture is filtered and the solvent is removed by vacuum stripping. Distillation of the residue through a 3 inch microvigreaux column yields 55 g of 3,3-dimethyl-6-(2-hydroxyethyl)-bicyclo(2.2.2)octanone having the structure:

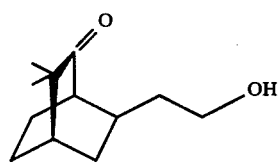

EXAMPLE III

Preparation of 3,3-dimethyl-6-(2-chloroethyl)-bicyclo (2.2.2)-octan-2-one

To a stirred solution of 50 g of 3,3-dimethyl-6-(2-hydroxyethyl)-bicyclo(2.2.2)-octan-2-one (produced according to Example II) in 200 ml of dry pyridine is added 30 g of thionyl chloride. The mixture is stirred at 50° C for 2 hours and then poured into 50 g of water. The resulting aqueous solution is extracted with three 200 ml portions of ether. The combined ether layers are washed with two 100 ml portions of 5% aqueous HCl and dried over anhydrous sodium sulfate. The ether is stripped and the residue is vacuum distilled, yielding about 42 g of 3,3-dimethyl-6-(2-chloroethyl)-bicyclo(2.2.2)-octan-2-one, having the structure:

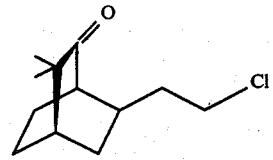

EXAMPLE IV

Preparation of 8,8-dimethyloctahydro-1,5-methano-1H-inden-1-ol

A sodium sand is prepared by heating 8 g of sodium to 110° C in 20 ml of toluene and stirring rapidly while the mixture is cooled slowly to room temperature. The sodium sand is washed with two 30 ml portions of tetrahydrofuran. A mixture of 300 ml of tetrahydrofuran and 20 g of 3,3-dimethyl-6-(2-chloroethyl)-bicyclo (2.2.2)-octan-2-one (produced according to Example III) is added to the flask and the mixture is refluxed for 3 hours. The resulting organic layer is separated and dried over anhydrous sodium sulfate, and the solvent is removed by stripping under vacuum. The residue is vacuum distilled yielding about 10 g of a mixture the major component of which is 8,8-dimethyloctahydro-1,5-methanol-1H-inen-1-ol, having the structure:

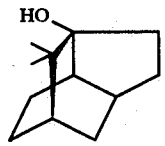

EXAMPLE V

Perfume Formulation

The following "woody cologne" perfume formulation is prepared:

| Ingredients | Parts by Weight |
|---|---|
| Bergamot Oil | 150 |
| Orange Oil | 200 |
| Lemon Oil | 50 |
| Eugenol | 10 |
| 4-(4-methyl-4-hydroxy amyl) 3cyclohexene carboxaldehyde | 40 |
| Ylang | 2 |
| Petitgrain Paraguay | 10 |
| Gamma methyl ionone | 20 |
| 3a-methyl-dodecahydro-6,6,9a-trimethylnaphtho-(2,1-b) furan | 5 |
| Product produced by reaction of acetic anhydride, polyphosphoric acid and 1,5,9-trimethyl cyclododecatriene-1,5,9 according to the process of Example I of U.S. Patent 3,718,697 | 5 |
| 8,8-dimethyloctahydro-1,5-methano-1H-inden-1-ol produced according to Example IV | 15 |

8,8-Dimethyloctahydro-1,5-methano-1H-inden-1-ol imparts a warm patchouli-like character to this "woody colonge" composition.

EXAMPLE VI

Preparation of a Soap Composition

A total of 100 g of soap chips produced from unperfumed sodium base toilet soap made from tallow and coconut oil are mixed with 1 g of the perfume composition set forth in Example V until a substantially homogeneous composition is obtained. The soap composition manifests a characteristic "woody cologne" aroma having a warm patchouli-like character.

EXAMPLE VII

Preparation of a Soap Composition

A total of 100 g of soap chips produced from unperfumed sodium base toilet soap made from tallow and coconut oil is mixed with 1 g of 8,8-dimethyloctahydro-1,5-methano-1H-inden-1-ol until a substantially homogeneous composition is obtained. The soap composition manifests a warm patchouli-like character.

EXAMPLE VIII

Preparation of a Detergent Composition

A total of 100 g of a detergent powder sold under the trademark "RINSO" are mixed with 0.15 g of a perfume composition containing the mixture obtained in Example V until a substantially homogeneous composition having a "woody cologne" fragrance with a warm patchouli-like character is obtained.

EXAMPLE IX

Preparation of a Cosmetic Base

A cosmetic powder is prepared by mixing 100 g of talcum powder with 0.25 g of the perfume composition of Example V in a ball mill. A second cosmetic powder is similarly prepared except that the mixture produced in Example V is replaced with the product produced in Example IV, 8,8-dimethyloctahydro-1,5-methano-1H-inden-1-ol. The cosmetic powder containing the material of Example V has a "woody cologne" fragrance with a warm patchouli-like character. The cosmetic powder produced using this material of Example IV has a warm natural patchouli-like character.

EXAMPLE X

Liquid Detergent Containing 8,8-dimethyloctahydro-1,5-methano-1H-inden-1-ol

Concentrated liquid detergents with a patchouli like odor containing 0.2, 0.5 and 1.2% of the product produced in accordance with the process of Example IV, 8,8-dimethyloctahydro-1,5-methanol-1H-inden-1-ol are prepared by adding the appropriate quantity of 8,8-dimethyloctahydro-1,5-methano-1H-inden-1-ol to the liquid detergent known as P-87. The patchouli aroma of the liquid detergent increases with increasing concentration of the 8,8-dimethyloctahydro-1,5-methano-1H-inden-1-ol of this invention.

EXAMPLE XI

Preparation of Cologne and Handkerchief Perfume

The composition of Example VIII is incorporated in a cologne having a composition of 2.5% in 85% aqueous ethanol; and into a handkerchief perfume in a concentration of 20% (in 95% ethanol). The use of the composition of Example V affords a distinct and definite "woody cologne" aroma having a warm patchouli-like character to the handkerchief perfume and to the cologne.

EXAMPLE XII

Cologne and Handkerchief Perfume

The 8,8-dimethyloctahydro-1,5-methano-1H-inden-1-ol produced by the process of Example IV is incorporated into a cologne having a concentration of 2.5% in 85% ethanol; and into a handkerchief perfume in a concentration of 10% (in 95% ethanol). The 8,8-dimethyloctahydro-1,5-methanol-1H-inden-1-ol produced in Example IV affords a distinct and definite warm patchouli-like aroma to the handkerchief perfume and to the cologne.

EXAMPLE XIII

Flavor Composition

The following basic walnut flavor formulation is prepared:

| Ingredients | Parts by Weight |
|---|---|
| Ethyl-2-methyl butyrate | 10 |
| Vanillin | 40 |
| Butyl valerate | 40 |
| 2,3-Diethyl pyrazine | 5 |
| Methyl cyclopentenolone | 80 |
| Benzaldehyde | 60 |
| Valerian oil Indian | 0.5 |
| (1% in 95% aqueous ethanol alcohol) | |
| Propylene Glycol | 764.5 |

8,8-dimethyloctahydro-1,5-methano-1H-inden-1-ol produced by the process of Example IV is added to the above formulation at the rate of 1.5%. This formulation is compared to a formulation which does not have 8,8-dimethyloctahydro-1,5-methano-1H-inden-1-ol added to it, at the reate of 20 ppm in water. The formulation containing 8,8-dimethyloctahydro-1,5-methanol-1H-inden-1-ol has a "woody-balsamic", fresh walnut kernel and walnut skin-like taste and, in addition, has a fuller mouthfeel and longer lasting taste. The flavor that has added to it, 8,8-dimethyloctahydro-1,5-methano-1H-inden-1-ol is preferred by a group of flavor panelists, and they consider it to be a substantially improved walnut flavor.

EXAMPLE XIV

Beverage

The addition of 8,8-dimethyloctahydro-1,5-methano-1H-inden-1-ol prepared by the process of Example IV at the rate of 0.3 ppm to a commercial Cola beverage gives the beverage a fuller "woody-balsamic" long lasting taste and adds to the pleasant top notes of the beverage. When comparing the Cola beverage containing 8,8-dimethyloctahydro-1,5-methano-1H-inden-1-ol to one having the same formula but not containing 8,8-dimethyloctahydro-1,5-methano-1H-inden-1-ol, a five member bench panel prefers the beverage containing the 8,8-dimethyloctahydro-1,5-methano-1H-inden-1-ol.

EXAMPLE XV

Tobacco Flavor Formulation

Cigarettes are produced using the following tobacco formulation:

| Ingredients | Parts by Weight |
|---|---|
| Bright | 40.1 |
| Burley | 24.9 |
| Maryland | 1.1 |
| Turkish | 11.6 |

| Ingredients | Parts by Weight |
| --- | --- |
| Stem (flue-cured) | 14.2 |
| Glycerine | 2.8 |
| H₂O | 5.3 |

At the rate of 0.2%, the following tobacco flavor formulation is applied to all of the cigarettes produced with the above tobacco formulation.

| Ingredients | Parts by Weight |
| --- | --- |
| Ethyl butyrate | .05 |
| Ethyl valerate | .05 |
| Maltol | 2.00 |
| Cocoa Extract | 26.00 |
| Coffee Extract | 10.00 |
| Ethyl Alcohol (95%) | 20.00 |
| H₂O | 41.90 |

To 50% of the cigarettes, 10 and 20 ppm of 8,8-dimethyloctahydro-1,5-methanol-1H-inden-1-ol are added. These cigarettes are hereinafter called "experimental"-cigarettes and the cigarettes without the 8,8-dimethyloctahydro-1,5-methano-1H-inden-1-ol are hereinafter called "control" cigarettes. The control and experimental cigarettes are then evaluated by paired comparison and the results are as follows:

a. In Aroma, the experimental cigarettes are found to be more aromatic.

b. In smoke flavor, the experimental cigarettes are found to be more aromatic, more sweet, more bitter, more green, richer and slightly less harsh in the mouth and more cigarette tobacco-like than the control cigarettes.

The experimental cigarettes containing 20 ppm of 8,8-dimethyloctahydro-1,5-methano-1H-inden-1-ol are found to be woody, slightly chemical and mouth-coating in the smoke flavor.

All cigarettes both control and experimental, are evaluated for a smoke flavor with 20 mm cellulose acetate filter. 8,8-Dimethyloctahydro-1,5-methano-1H-inden-1-ol enhances the tobacco-like taste of the blended cigarette.

EXAMPLE XVI

Preparation of 1,3,3-trimethyl-6-(2-hydroxyethyl) bicyclo(2.2.2)-octa-5,7-dien-2-one An autoclave is charged with 20 g trimethyl cyclohexadienone, 20 g of 3-butyn-1-ol and 300 ml benzene. The autoclave is then sealed and the contents are heated to a temperature of 200°-210° C over a period of 2.5 hours. The autoclave is then cooled and the contents removed. The benzene is stripped off and the reaction product is vacuum distilled through a 3 inch microvigreaux column yielding two fractions of desired product weighing 26.8 grams, consisting of two components in a proportion of 59:28. The major component having the structure:

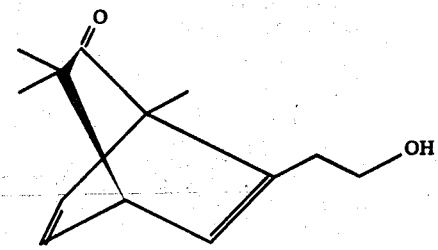

is distilled at 67°-70° C at a pressure of 7.0-12 mm Hg pressure.

EXAMPLE XVII

Preparation of 1,3,3-trimethyl-6-(2-hydroxyethyl) bicyclo(2.2.2)-octan-2-one

An autoclave is charged with 26.8 grams of 1,3,3-trimethyl-6-(2-hydroxyethyl)bicyclo(2.2.2)-octa-5,7-dien-2-one prepared according to the process of Example XVI, 2 grams 5% palladium/carbon catalyst, and 300 ml isopropyl alcohol. The autoclave is then sealed and pressurized with hydrogen to 400 psig, heated to 150° C and maintained at that temperature, with stirring, for a period of 48 hours. At the end of this period of time, the autoclave is opened and the reaction mass is removed. The reaction mass is filtered, and the excess isopropyl alcohol is stripped therefrom. The reaction product (the title product) is distilled at 64°-65° C at a pressure of 0.2 mm Hg (yield: 12.3 g). Its structure, confirmed by NMR and mass spectral analyses is as follows:

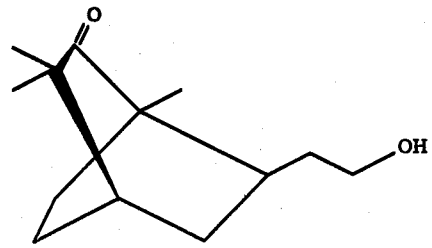

NMR Analysis: δ, 0.92(s,3H), 1.08(s,3H), 1.12(s,3H), 1.16-2.10(m,10H), 3.64(m,2H) ppm.

Mass spectral analysis (in decreasing intensity): m/e = 82, 41, 138, 55, 210(m).

EXAMPLE XVIII

Preparation of 1,3,3-trimethyl-6(2-chloroethyl)bicyclo(2.2.2)-octan-2-one

To a 100 ml microflask equipped with thermometer, reflux condenser, dropping funnel and magnetic stirrer is charged 12.3 g of 1,3,3-trimethyl-6-(2-hydroxyethyl) bicyclo(2.2.2)-octan-2-one prepared according to the process of Example XVII, and 20 ml benzene. The dropping funnel is charged with 12 g thionyl chloride. The thionyl chloride is added to the reaction mass from the dropping funnel, slowly, over a period of five minutes as the temperature of the reaction mass rises to 35° C. The reaction mass is then refluxed for a period of 10 hours at 90° C. The flask is then vented to the atmosphere and heated on a steam bath in order to volatilize the unreacted thionyl chloride and any hydrogen chloride reaction product remaining. The reaction mass is then cooled and hydrolyzed with 50 g ice. The organic layer is separated, and the aqueous phase is extracted with four 20 ml portions of anhydrous diethyl ether. The organic layers are bulked and washed with (i) three 20 ml portions of saturated sodium bicarbonate solution and (ii) one 20 ml portion of water. The organic phase is then dried over anhydrous magnesium sulfate and stripped of the diethyl ether. The reaction product is then distilled at 105°–115° C at a pressure of 0.2 mm Hg. Its structure, confirmed by NMR and mass spectral analyses is as follows:

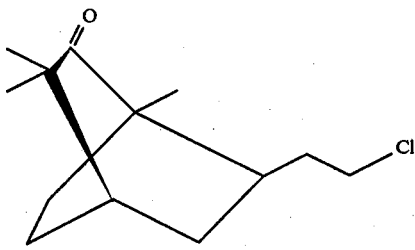

NMR Analysis: δ, 0.92(s,3H), 1.08(s,3H), 1.15(s,3H), 1.44–2.17(m,10H), 3.55(m,2H) ppm Mass Spectral Analysis (in decreasing intensity): m/e = 156, 82, 157, 41, 93.

EXAMPLE XIX

Preparation of octahydro-7A,8,8-trimethyl-1,5-methano-1H-inden-1-ol

A sodium sand is formed by placing 7 grams of sodium spheres into a 500 ml flask fitted with reflux condenser, thermometer and nitrogen inlet; along with 15 ml toluene. The resulting slurry is heated to reflux (90° C) with stirring, until the sodium is dispersed into fine particles. An ice bath is applied at the same time that stirring is ceased; and the sodium is thereby cooled in the particulate state. The resulting sodium dispersion is then washed with two 15 ml portions of tetrahydrofuran in order to remove the toluene.

The reaction vessel containing the resulting sodium sand is then charged with 300 ml tetrahydrofuran and 7.6 g of 1,3,3-trimethyl-6-(2-chloromethyl) bicyclo(2.2.2)-octan-2-one prepared according to the process of Example XVIII and heated to reflux for a period of 5 hours. During the reflux period, the sodium dispersion remains as such and does not coagulate. The reaction mixture remains at room temperature for a period of 12 hours and is then filtered to remove unreacted sodium metal. The reaction mixture is then acidified with 5% aqueous HCl to a pH of 3 in order to form the alcohol; and then neutralized to a pH of 7.8 with a saturated sodium bicarbonate solution. The resulting organic layer is separated from the aqueous layer and the aqueous layer is "back-extracted" with four 75 ml portions of anydrous diethyl ether after which all the organic layers are bulked.

The bulked organic layers are then washed with 75 ml water; and then dried over anhydrous magnesium sulfate. The excess diethyl ether is then stripped off a rotary evaporator, and the product is vacuum distilled using a micro-rushover apparatus. Four fractions are obtained, three of which contain a reasonable amount of desired product, as follows:

| Fraction | % Title Product | Distillation Condition |
|---|---|---|
| 2 | 45% | 88° C; 0.6 mm Hg |
| 3 | 62% | 107° C; 0.6 mm Hg |
| 4 | 42% | 120° C; 0.6 mm Hg |

Fractions "3" becomes partially crystalline on standing. Fraction "3" is chromatographed on a column of 20 grams of silica gel and eluted with a 4:1 mixture of pentane:diethyl ether. Pure title product is obtained in the seventh chromatography fraction, and is confirmed by mass spectral, NMR and infra-red analyses to have the structure:

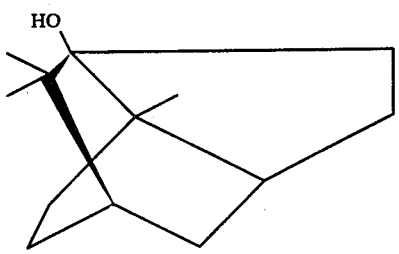

NMR Analysis: δ, 0.80(s,3H), 1.02(s,3H), 1.09(s,3H), 1.10–2.30(m,12)ppm.

Mass Spectral Analysis (in decreasing intensity): m/e = 41, 43, 110, 39, 194(m).

The title product has a strong, slightly nutty, sweet, warm, earthy, woody, camphoraceous fragrance note; an earthy, patchouli, woody, camphoraceous flavor aroma and a patchouli, earthy, red peat-like, nutty and woody taste.

EXAMPLE XX

ORIENTAL PERFUME FORMULATION

The following mixture is prepared:

| Ingredient | Parts by Weight |
|---|---|
| Orange Oil | 200 |
| Bergamot Oil | 150 |
| Lemon Oil | 30 |
| Orange Flower, Absolute | 20 |
| Neroli Oil | 30 |
| 4-(4-Methyl-4-hydroxyamyl) 3-cyclohexene carboxaldehyde | 50 |
| Rose Absolute | 5 |
| Octahydro-7A,8,8-trimethyl-1,5-methano-1H-inden-1-ol (prepared according to the process of Example XIX, supra) | 30 |
| Ylang, Extra | 5 |
| Petitgrain, Absolute | 100 |
| 1',2',3',4',5',6',7',8'-octahydro 2',3',8',8'-tetramethyl-2'-acetonaphthone isomer mixture produced according to the process of Example VII of Application for U.S. Letters Pat. No. 434,948 filed on January 21, 1974 | 40 |
| Gamma Methyl Ionone | 20 |
| Indole | 2 |
| Indolene | 5 |
| Labdanum, Absolute | 5 |
| Benzoin, Coeur | 30 |
| Myrrh, Coeur | 10 |

The octahydro-7A,8,8-trimethyl-1,5-methano-1H-inden-1-ol produced according to the process of Example XIX, when added to this formulation in the amount indicated; and also in amounts up to 30% by weight of the total mixture; or in amounts as little as 1.0% by weight of this mixture, imparts a warm, patchouli character thereto, essential for the woody, oriental note in this oriental perfume composition.

EXAMPLE XXI

Preparation of a Soap Composition

A total of 100 g of soap chips produced from unperfumed sodium base toilet soap made from tallow and coconut oil is mixed with 1 g of octahydro-7A,8,8-trimethyl-1,5-methano-1H-inden-1-ol (produced according to Example XIX) until a substantially homogeneous composition is obtained. The soap composition manifests a warm patchouli-like character having earthy, woody and camphoraceous notes.

EXAMPLE XXII

Preparation of a Detergent Composition

A total of 100 g of a detergent powder sold under trademark "RINSO" are mixed with 0.15 g of a perfume composition containing the mixture prepared according to Example XX until a substantially homogeneous composition having a "woody-oriental" fragrance with a warm patchouli-like character is obtained.

EXAMPLE XXIII

Preparation of a Cosmetic Base

A cosmetic powder is prepared by mixing 100 g of talcum powder with 0.25 g of the perfume composition of Example XX in a ball mill. A second cosmetic powder is similarly prepared except that the mixture produced in Example XX is replaced with the product produced in Example XIX, octahydro-7A,8,8-trimethyl-1,5-methano-1H-inden-1-ol. The cosmetic powder containing the material of Example XX has a "woody-oriental" fragrance with a warm patchouli-like character. The cosmetic powder produced using the material of Example XIX has a warm natural patchouli-like character with earthy, woody and camphoraceous notes.

EXAMPLE XXIV

Liquid Detergent Containing Octahydro-7A,8,8-Trimethyl-1,5-Methano-1H-Inden-1-OL Concentrated liquid detergents with a warm patchouli-like odor having earthy, woody and camphoraceous notes containing 0.2, 0.5 and 1.2% of the product produced in accordance with the process of Example XIX, octahydro-7A,8,8-trimethyl-1,5-methano-1H-inden-1-ol, are prepared by adding appropriate quantities of octahydro-7A,8,8-trimethyl-1,5-methano-1H-inden-1-ol to the liquid detergent known as P-87. The warm patchouli aroma of the liquid detergent increases with increasing concentration of the octahydro-7A-8,8-trimethyl-1,5-methano-1H-inden-1-ol of this invention.

EXAMPLE XXV

Preparation of Cologne and Handkerchief Perfume

The composition of Example XX is incorporated in a cologne having a concentration of 2.5% in 85% aqueous ethanol; and into a handkerchief perfume in a concentration of 20% (in 95% aqueous ethanol). The use of the composition of Example XX affords a distinct and definite "woody-oriental" aroma having a warm patchouli-like character to the handkerchief perfume and to the cologne.

EXAMPLE XXVI

Cologne and Handkerchief Perfume

The octahydro-7A,8,8-trimethyl-1,5-methano-1H-inden-1-ol produced by the process of Example XIX is incorporated into a perfume having a concentration of 2.5% in 85% ethanol; and into a handkerchief perfume in a concentration of 10% (in 95% aqueous ethanol). The octahydro-7A,8,8-trimethyl-1,5-methanol-1H-inden-1-ol produced in Example XIX affords a distinct and definite warm patchouli-like aroma (with earthy, woody and camphoraceous notes) to the handkerchief perfume and to the cologne.

EXAMPLE XXVII

Flavor Composition

The following basic walnut flavor formulation is prepared:

| Ingredients | Parts by Weight |
| --- | --- |
| Ethyl-2-methyl butyrate | 10 |
| Vanillin | 40 |
| Butyl valerate | 40 |
| 2,3-Diethyl pyrazine | 5 |
| Methyl cyclopentenolone | 80 |
| Benzaldehyde | 60 |
| Valerian oil Indian (1% in 95% aqueous ethanol alcohol) | 0.5 |
| Propylene Glycol | 764.5 |

Octahydro-7A,8,8-trimethyl-1,5-methano-1H-inden-1-ol produced by the process of Example XIX is added to the above formulation at the rate of 1.5%. This formulation is compared to a formulation which does not have octahydro-7A,8,8-trimethyl-1,5-methano-1H-inden-1-ol added to it, at the rate of 20 ppm in water. The formulation containing octahydro-7A,8,8-trimethyl-1,5-methano-1H-inden-1-ol has a "woody-balsamic", fresh walnut kernel and walnut skin-like taste, and in addition, has a fuller mouthfeel and longer lasting taste. The flavor that has added to it, octahydro-7A,8,8-trimethyl-1,5-methano-1H-inden-1-ol is preferred by a group of flavor panelists, and they consider it to be a substantially improved walnut flavor.

EXAMPLE XXVIII

Beverage

The addition of octahydro-7A,8,8-trimethyl-1,5-methano-1H-inden-1-ol prepared by the process of Example XIX at the rate of 0.3 ppm to a commercial Cola beverage gives the beverages a fuller "woody-balsamic" long lasting taste and addes to the pleasant top notes of the beverage. When comparing the Cola beverage containing octahydro-7A,8,8-trimethyl-1,5-methano-1H-inden-1-ol to one having the same formula but not containing octahydro-7A,8,8-trimethyl-1,5-methano-1H-inden-1-ol, a five member bench panel prefers the beverage containing the octahydro-7A,8,8-trimethyl-1,5-methano-1H-inden-1-ol.

EXAMPLE XXIX

Tobacco Flavor Formulation

Cigarettes are produced using the following tobacco formulation:

| Ingredients | Parts by Weight |
| --- | --- |
| Bright | 40.1 |

| Ingredients | Parts by Weight |
|---|---|
| Burley | 24.9 |
| Maryland | 1.1 |
| Turkish | 11.6 |
| Stem (flue-cured) | 14.2 |
| Glycerine | 2.8 |
| $H_2O$ | 5.3 |

At the rate of 0.2%, the following tobacco flavor formulation is applied to all of the cigarettes produced with the above tobacco formulation.

| Ingredients | Parts by Weight |
|---|---|
| Ethyl butyrate | .05 |
| Ethyl valerate | .05 |
| Maltol | 2.00 |
| Cocoa Extract | 26.00 |
| Coffee Extract | 10.00 |
| Ethyl Alcohol (95%) | 20.00 |
| $H_2O$ | 41.90 |

To 50% of the cigarettes, 10 and 20 ppm of octahydro-7A,8,8-trimethyl-1,5-methano-1H-inden-1-ol are added. These cigarettes are hereinafter called "experimental" cigarettes and the cigarettes without the octahydro-7A,8,8-trimethyl-1,5-methano-1H-inden-1-ol are hereinafter called "control" cigarettes. The control and experimental cigarettes are then evaluated by paired comparison and the results are as follows:

a. In aroma, the experimental cigarettes are found to be more aromatic.
b. In smoke flavor, the experimental cigarettes are found to be more aromatic, more sweet, more bitter, more green, richer and slightly less harsh in the mouth and more cigarette tobacco-like than the control cigarettes.

The experimental cigarettes containing 20 ppm of octahydro-7A,8,8-trimethyl-1,5-methano-1H-inden-1-ol are found to be woody, slightly chemical and mouth-coating in the smoke flavor.

All cigarettes both control and experimental, are evaluated for a smoke flavor with 20 mm cellulose acetate filter. Octahydro-7A,8,8-trimethyl-1,5-methano-1H-inden-1-ol enhances the tobacco-like taste of the blended cigarette.

EXAMPLE XXX 1,5-Methano-1H-inden-1-ol, octahydro-7A,8,8-trimethyl (I) Versus Pathchouli Alcohol Chemical I has a warm, earthy, camphoraceous note with amber, woody nuances. This material is useful as a patchouli-like note for use in perfumes. Although it has a great deal of patchouli character, it lacks the very diffusive top note of patchouli alcohol. On the other hand, it seems at least as strong as patchouli alcohol as it dries out.

The patchouli effect rendered by this chemical (I) may be demonstrated in the following fragrance wherein it replaces patchouli alcohol, but is used at a slightly higher concentration.

| Ingredient | A | B |
|---|---|---|
| Linalool | 70 | 70 |
| Linalyl acetate | 20 | 20 |
| Benzyl acetate | 20 | 20 |
| Citronellol | 10 | 10 |
| Geraniol | 60 | 60 |
| Phenylethyl alcohol | 110 | 110 |
| Hydroxy citronellal | 40 | 40 |
| Cedryl acetate | 170 | 170 |
| Eugenol | 20 | 20 |
| Sandalwood oil | 40 | 40 |
| Diethyl phthalate | 72 | 22 |
| Hexyl cinnamic aldehyde | 10 | 10 |
| Coumarin | 20 | 20 |
| Musk xylol | 40 | 40 |
| Musk ambrette | 50 | 50 |
| Bergamot oil | 13 | 13 |
| Ethyl vanillin | 4 | 4 |
| Phenylethyl acetate | 10 | 10 |
| Amyl salicylate | 21 | 21 |
| Benzyl salicylate | 100 | 100 |
| Patchouli alcohol (II) | 100 | — |
| Chemical I | — | 150 |
| | 1000 | 1000 |

The replacement of Chemical I for patchouli alcohol in the above formulation changes somewhat the overall character of the fragrance. A different type of patchouli effect is obtained. This effect, which is more warm, woody, is very pleasing and has a desirable character. To those versed in the art, this new patchouli effect can be more desirable than that obtained when using patchouli alcohol. Chemical I may be used in fragrances at from 0.1 up to 25% by weight. Higher concentrations, up to 75% may be used to obtain certain effects, especially to create patchouli-like specialties.

What is claimed is:

1. A compound having the structure:

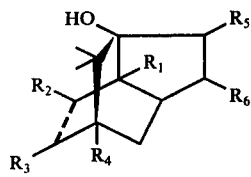

wherein each of $R_1$, $R_2$, $R_3$, $R_4$, $R_5$ and $R_6$ is selected from the group consisting of hydrogen and methyl; wherein the dashed line is a carbon-carbon single bond or a carbon-carbon double bond; and wherein when the dashed line is a carbon-carbon single bond, one of $R_2$ or $R_3$ is hydrogen.

2. The compound of claim 1 wherein $R_1$, $R_2$, $R_3$, $R_4$, $R_5$ and $R_6$ is each hydrogen, and the dashed line is a single bond.

3. The compound of claim 1 wherein $R_1$ is methyl and $R_2$, $R_3$, $R_4$, $R_5$ and $R_6$ is each hydrogen and the dashed line is a single bond.

* * * * *

UNITED STATES PATENT OFFICE
CERTIFICATE OF CORRECTION

Patent No. 4,041,084      Dated August 9, 1977

Inventor(s) Kenneth K. Light; Edward J. Shuster; Joaquin F. Vinals; Manfred Hugo Vock It is certified that error appears in the above-identified patent and that said Letters Patent are hereby corrected as shown below:

Column 2, top structure:

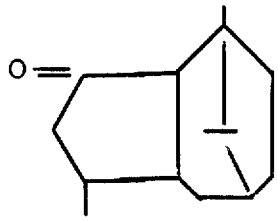

should read

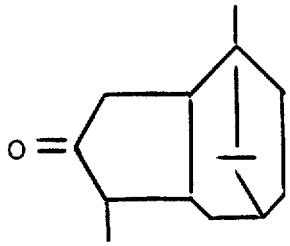

Signed and Sealed this

First Day of August 1978

[SEAL]

Attest:

RUTH C. MASON
*Attesting Officer*

DONALD W. BANNER
*Commissioner of Patents and Trademarks*